United States Patent [19]

Gross

[11] 3,975,342

[45] Aug. 17, 1976

[54] TYROSYL-CLASS ANTIGENIC CONJUGATES, THEIR PREPARATION AND ANTIBODIES RAISED THERETO

[75] Inventor: Stanley Joseph Gross, Encino, Calif.

[73] Assignee: Biological Developments, Inc., Encino, Calif.

[22] Filed: Mar. 18, 1974

[21] Appl. No.: 451,812

Related U.S. Application Data

[63] Continuation-in-part of Ser. No. 253,632, May 15, 1972, abandoned, which is a continuation-in-part of Ser. No. 89,929, Nov. 16, 1970, abandoned, which is a continuation-in-part of Ser. No. 45,558, June 11, 1970, abandoned.

[52] U.S. Cl. ................... 260/112 R; 260/78 A; 260/112 B; 260/112.5 R; 260/121; 424/8; 424/12; 424/85; 424/88; 424/177
[51] Int. Cl.² ............. A61K 37/00; C07C 103/52; C07G 69/36; G01N 31/00
[58] Field of Search ............ 424/8, 11, 12, 13, 177, 424/85, 88; 260/112 R, 112 B, 112.5, 121, 192, 207, 78 A

[56] References Cited

UNITED STATES PATENTS 3,809,782  5/1974  Spector .................. 424/12 X

OTHER PUBLICATIONS

Gross, Immunochem., vol. 5, 1968, pp. 55–65.
Spector, Advances in Biochem. Psychopharm., vol. 1, 1969, pp. 181–190.
Churchill, Nature, vol. 202, 1964, pp. 29–31.
Peskar, Science, vol. 179, Mar. 30, 1973, pp. 1340–1341.

*Primary Examiner*—V. D. Turner
*Assistant Examiner*—A. P. Fagelson
*Attorney, Agent, or Firm*—McAulay, Fields, Fisher & Goldstein

[57] ABSTRACT

Tyrosyl, thyronine, and histidyl compounds of the formulas:

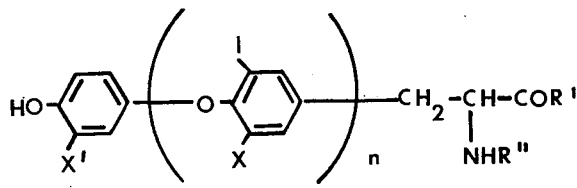

and

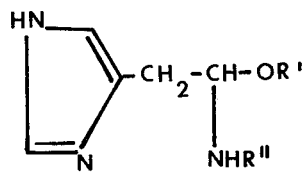

where R' is selected from the group consisting of —OH and —NHP$_p$, and R'' is selected from the class consisting of —H and —COP$_p$, where P$_p$ is a polypeptide chain having from 1 to 250 peptide groups, with or without pendant groups, X is selected from the class consisting of H and I; when X is I, X' is selected from the group consisting of H and I; and n is 0 or 1, where X' is H when n is 0; are conjugated to a carrier by first forming a primary aromatic amine on the carrier, diazotizing the amine, and coupling the tyrosyl, histidyl, or thyronine through the diazo group to form a novel antigenic conjugate. This novel antigenic conjugate can be injected into an animal for production of specific antibodies which are useful in assaying for the target, particularly by radioassaying.

21 Claims, No Drawings

TYROSYL-CLASS ANTIGENIC CONJUGATES, THEIR PREPARATION AND ANTIBODIES RAISED THERETO

CROSS-REFERENCES TO RELATED APPLICATIONS

This application is a continuation-in-part of my co-pending application Ser. No. 253,632, filed May 15, 1972, now abandoned, which was a continuation-in-part of co-pending application Ser. No. 89,929, filed Nov. 16, 1970, now abandoned, which, in turn, was a continuation-in-part of my application Ser. No. 45,558, filed June 11, 1970, now abandoned.

BACKGROUND OF THE INVENTION

1. Field of the Invention

This invention relates to immunoassaying. Immunoassayings are proving of immense value in medicine and biology for the assaying of the constituents of biological fluids, because of the sensitivity and specificity of such assaying. In immunoassaying procedures, for a given target compound, a synthetic antigen is generally first prepared. Heretofore, this has usually been accomplished by coupling the target compound, or a closely related compound, through a coupling group to a carrier which confers antigenicity to the entire compound. The compound coupled to the carrier is usually known as a hapten and, when coupled, it functions as an antigen determinant by causing the antibodies produced to be specific to it. Thus, the antibodies produced have a distinct and unique character, such that they will bind with only a specific compound or class of compounds. The objective in devising the synthetic antigen-hapten conjugate is to provide a compound which will generate antibodies that are specific to the target compound.

Antibodies are prepared by injecting the synthetic hapten-antigen conjugate into mammals and recovering blood serum from the mammals after they have had time to generate antibodies. Typical mammals are rabbits and goats.

The principal problem is usually synthesizing antigens that are capable of producing antibodies that are sufficiently specific. Biological fluids such as blood and urine frequently contain very closely related compounds and it is common for antibodies to be unable to distinguish the target compound from close relatives, or sometimes even distant ones. The antibody is then considered to be a poor one and is said to have low specificity and high cross-reactivity.

The assay itself is commonly a competitive binding assay. In such an assay, the target compound, which is not necessarily extracted, is allowed to compete with known quantities of a labeled standard to bind with a known quantity of specific antibody. From measurement of the proportion of the labeling in the standard-antibody complex that results, the amount of target compound present can be calculated. Radioactive labeling is particularly convenient. Fluorescence perturbation can be used. Normally it will be necessary to remove any unreacted labeled standard, before making the determination on the antibody complex.

Thyronines include compounds of fundamental importance to the functioning of the thyroid gland namely triiodothyronine ($T_3$) and thyroxine ($T_4$) or tetraiodothyronine. Accurate assay of these compounds is essential in understanding, detecting and controlling thyroid disorders. Other compounds of interest in this class are glucagon and thyroid releasing hormone.

THE PRIOR ART

The cross-referenced applications disclose inter alia hapten-antigen conjuages in which a hapten is coupled to an antigen through a diazo group, a phenyl ring and an amide bond to a proteinic antigen. Numerous haptens are disclosed and steroids are of particular interest.

A process for coupling glucagon to a protein carrier, in a one-step process, involving the conjunct reaction of glucagon and the protein with bis-diazotized benzidine is described by Senyk et al, "Immunochemistry," Vol. 9, pp. 97–110. The coupling scheme employed is, however, quite different from that to be used here.

C. S. Hollander, "Hospital Practice," May 1972, p. 87 discloses conjugates of $T_3$ and $T_4$ with antigenic proteins, but does not disclose the nature of the couple between the hapten and antigen or how the conjugates are synthesized.

Similarly, Dunn et al, "Clin. Chem.," 1919, 1063–1066 (1973) and Gharib et al, "Rapid Communication," Dec. 1970, p. 709 report $T_3$ or $T_4$ conjugates but do not completely disclose the nature of the couple or the synthesis. Gharib refers to succinylated polylysine but gives no details. The succinyl group has no diazo bridge.

A hapten-antigen conjugate, synthesized by coupling a linking group to a proteinic antigen, followed by diazotizing of the linking group into the hapten, is described in Peskor and Spector, "Science,"Vol. 179, pp. 1340–41 of March 30, 1973. The hapten employed, according to that article, is serotonin, quite different from the haptens employed according to the present invention. The serotonin has a number of possible diazotizable sites, by contrast to the clearly defined sites of the compounds of the present invention and, thus, the specific antibody, which is desired, is unlikely to be produced as it is according to the present invention.

BRIEF DESCRIPTION OF THE INVENTION

In accordance with the present invention, antigenic conjugates are formed from materials of formulas:

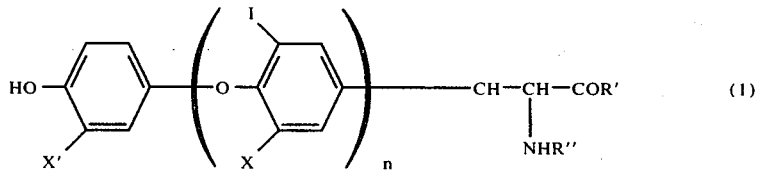    (1)

and

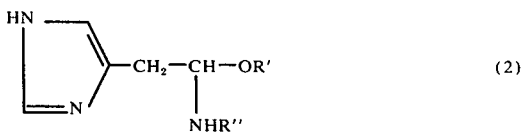    (2)

where R' is selected from the group consisting of —OH and —NHP$_p$ and R" is selected from the class consisting of —H and —COP$_p$, where P$_p$ is a polypeptide chain having from 1 to 250 peptide groups, with or without pendant groups; X is selected from the class consisting of H and I; X' is selected from the class consisting of H and I when X is I; and n is 0 or 1 and X' is H when n is 0; and a carrier on which a diazo group has been formed.

The materials defined by formulas (1) and (2) above have the distinctive tyrosyl group, the closely related histidyl compounds which differ from the tyrosyl in having a five-membered, heterocyclic nitrogen-containing ring in place of the tyrosyl hydroxyphenyl ring and, also, include the closely related iodinated thyronine compounds, and their important iodo-substituents. All these compounds have a phenyl (or in the case of histidyl, phenyl-like) ring carrying, at one end, an accessible, moderately reactive group on either side of which there is a tertiary carbon atom that is susceptible to diazonium coupling. Further, the opposite side of the ring is connected to an amine-substituted propionic residue. In the case of the thyronine compounds, this connection is through an iodine-substituted oxyphenyl group and the propionic residue is the acid with a simple amine substituent. Other than, of course, being an antigenic determinant, the iodine-substituted oxyphenyl bridge is substantially inactive in the conditions encountered in practicing the present invention. The tyrosyl and histidyl compounds of principal interest have one or two polypeptide groups attached to the propionic residue. The molecular weight of the polypeptides can be up to about 25,000, and natural polypeptides are of particular interest.

Many polypeptide compounds within the tyrosyl class will have a plurality of tyrosyl or histidyl groups, and some may have both. Examples of compounds having molecular weights below 4,000 and from 15 to 35 peptide groups are gastrin, particularly human, glucagon, particularly porcine, secretin, particularly porcine, and calcitonin, particularly human. Some gonadotropins have substantial numbers of both tyrosyl and histidyl groups together with approximately 200 peptide groups; examples are human growth hormone. Other compounds within the class include thyrotropin release hormone, chorionic gonadotropin, follicle stimulating hormone, thyrotropin releasing factor, human Australia antigen, parathyroid hormone, and adrenocorticotropic hormone.

In a broad aspect the invention comprises a process of preparing a synthetic antigenic conjugate comprising conjugating a primary aromatic amine with a carrier, the conjugation being effected to a residual part of the primary aromatic amine leaving the amino group available, diazotizing the available amine group, and coupling a tyrosyl-class hapten at an unsubstituded ring carbon to the diazo group of the carrier-diazonium conjugate to form a carrier-aryldiazo-(tyrosyl-class hapten) conjugate.

In general the diazo coupled hapten-carrier conjugates of this invention can generate antibodies specific to the hapten used in their preparation. However, in the cases of the use of a thyronine as the preparative hapten, it appears that the phenyldiazo group may be equivalent to, or provide an effective antigenic image of, an additional iodine atom so that the diiodothyronine antigenic conjugate raises antibodies specific to triiodothyronine (T$_3$) and the triiodothyronine antigenic conjugate raises antibodies specific for thyroxine (T$_4$) which is tetraiodothyronine.

In practice, an important step is thorough removal of small molecule products of the amine-conjugation step, prior to diazotization. One of the advantages of the process according to the present invention is that it becomes possible to couple the carrier to a hapten having reactive groups, particularly amino and carboxyl groups, that would take part in the carrier-coupling reaction were that reaction not performed before the introduction of the hapten into the reaction sequence. This is of particular merit for conjugating a tyrosyl-class hapten to a protein because the preferred coupling reactions with the protein are such as are likely to involve the reactive groups of the tyrosyl compound.

The carrier must have an available reactive group for coupling and the primary aromatic amine must have a suitably reactive residue to be coupled to the reactive group on the carrier. In one embodiment, the carrier can be a protein and the amine residue can carry a carboxyl group, the coupling then being effected with an amide bond.

The invention herein also relates to novel synthetic antigenic conjugates comprising a tyrosyl-class hapten coupled to an antigen through, respectively, a diazo group which is, in turn, connected to an aromatic ring.

DESCRIPTION OF THE PREFERRED EMBODIMENTS

In the description which follows, "the hapten" will refer to the tyrosyl-class hapten described above in formulas (1) and (2). In specific embodiments of the invention, the carrier can be proteinic, such as, for example, natural protein including bovine serum albumin (BSA), keyhole limpet hemocyanin (KLH), or human immunogammaglobulin (HGG), or a synthetic protein such as, for example, polylysine. The carrier can also be a polysaccharide, or other antigenic complex macromolecule. Although the carrier is usually immunogenic, it is not essential that it be so. It may be an incomplete antigen conferring antigenicity on the conjugate, i.e., the carrier is partially antigenic, but the conjugate is a complete antigen. The carrier should, however, preferably have some solubility in water or aqueous alcohol solution.

The primary aromatic amine should contain, in its residue, i.e., in the portion of the molecule other than the phenylamine moiety, a reactive group that can be used to couple it to the carrier. The particular reactive group will depend upon the nature of the carrier. With a proteinic carrier, there are a variety of coupling groups that can be used, and these will be illustrated in the specification to follow by reference to a carboxyl group which can conveniently be coupled to a free amine on the protein. It will be understood that other reactive groups and other carriers can also be employed.

The illustrative primary aminoaryloic acid can be any acid having a structure which satisfies, not only the already indicated requirement that the amino group shall be primary and connected directly to the phenyl ring, but also the requirements that the carboxyl group be sufficiently spaced from the amino group to permit coupling and that any other groups are innocuous in the process of the invention. Some additional groups that can be present are further phenyl rings, possibly conjugated with the first phenyl, and methylene groups.

It is conceivable that the advantages of the invention could be obtained with an aromatic amino acid having plural carboxylic groups, plural aminophenyl groups or even both pluralities, but no advantage is seen in such pluralities at present and it is contemplated by the present invention that such complications would be undesirable. Water solubility is desirable. The corresponding thio acids are also contemplated.

In the following detailed description, reference will be made to para-aminobenzoic acid, using the mneumonic "PABA," it being understood that other primary aromatic amine compounds can be used, provided they meet the above-mentioned requirements.

The novel conjugates of this invention have the following formula:

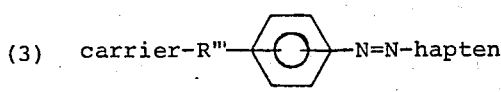

(3)

where the carrier confers antigenicity, the hapten is a tyrosyl-class hapten derived from the material of formulas (1) and (2), and R''' is a reactive group coupled to a reactive group on the carrier, the residue being essentially non-reactive in this sequence and being bonded to the aryl group at any position, preferably the meta positions remaining open, with one or more bonds. The R''' can be substituted or unsubstituted and can comprise a ring or aliphatic structure, or a combination of the two. Up to four rings are contemplated according to the present invention, naphthalene and biphenyl groups being examples of such ring structures. The aliphatic residue may contain up to 20 carbon atoms, preferably not more than 6.

The invention particularly contemplates conjugates in which the carrier molecule has a plurality of the indicated pendant hapten-terminating groups bonded to it.

Referring, particularly, to the process of the present invention, it comprises five steps:

1. Conjugation of a primary aromatic amine compound such as PABA, with the carrier.
2. Separation of the reactants from step 1.
3. Lyophilization (freeze-drying) of the residue from the separation to remove the reaction medium.
4. Diazotization.
5. Coupling of the hapten. The process of this invention provides a crude, normally aqueous mixture, which may contain not only the desired antigenic conjugate, but also the hapten and the reactants and reaction products of steps 4 and 5. Accordingly, it will normally be desirable to provide a purification step following step 5.

A detailed description of the various steps of the process, as outlined above, will follow:

Step 1: Conjugation of PABA with the Carrier

In this step, which includes a reaction generally well known in the art, a carrier amine group becomes combined with the PABA carboxyl to form an amide. In simple solution the carrier and PABA merely undergo some ionization to the corresponding substituted ammonium salt. Accordingly, to form the amide, the carboxyl group must be activated to remove its tendency to ionize and this can be done by substituting the hydroxyl hydrogen. In order to proceed to the amide the substituted PABA intermediate must be of moderate stability, certainly less stable than the amide.

One suitable and preferred acid-activating reactant is a carbodiimide. This is known to be effective and is thought to form a pseudourea intermediate. Other such reactants include isobutyl chloroformate and thionyl halides. This step of the process will be further described with reference to a carbodiimide, it being understood that other acid-activating reactants can be used.

The carrier is dissolved in water or aqueous methanol or ethanol, depending upon its solubility. The concentration is not critical, depending at the lower end of the possible range upon practical operating convenience and at the upper upon the solubility of the carrier. A particularly workable range is from about 1 to about 50 weight per cent of carrier to solution, with about 10 weight per cent being convenient. The solution is acidified with HCl to a pH of not less than about 3, preferably from 3.9 to 4.1.

The PABA product is dissolved in water or alcohol. Since its solubility is moderate, an excess can be used in suspension. The excess is taken up as the dissolved PABA product reacts; however, too great an excess should not be used, so that a practical limit is about 15 weight per cent PABA product to solvent. Convenience dictates a lower limit of about 0.5 weight per cent PABA product and a preferred range is from 1 to 10 weight per cent.

These two solutions, one of which may be a suspension, are mixed and carbodiimide is added as a solid. Preferably there is a slight stoichiometric excess, generally less than 5%, of carbodiimide over PABA product to maximize material usage.

The reaction mixture is then stirred for from 6 to 8 hours. The stirring can be continued longer, but 8 hours is normally sufficient for the reaction to go to completion. Some reaction should occur after about one hour.

In this step the temperature range is desirably from 4 to 25°C., but can extend beyond these limits provided that it does not go below about −10°C., in which case the solution might freeze, or above a temperature at which substantial decomposition of the carrier occurs. With a proteinic carrier, severe denaturing is likely to occur at about 60°C.

Step 2: Separation of the Reactants

It is highly important to remove any small molecule compounds, notably unreacted PABA or carbodiimide from step 1, before diazotization as they may interfere with diazotization. Furthermore, it is desirable to carry this removal to the practical limits of completion.

One way of effecting this removal is by dialysis against a mildly acid solution, e.g., 0.001N HCl. The dialysis is continued for from 2 to 10 days although 2 is likely to be inadequate and 10 unnecessary. Accordingly, 4 to 6 days is preferred. If the antigen is a protein, the temperature is kept reasonably low, to, for example, 4°C. since it is undesirable to keep aqueous proteins at room temperature for prolonged periods of time.

Step 3: Lyophilization

For convenience and control of the next step, it will normally be desirable to separate the antigen-PABA conjugate. Conveniently this is done by lyophilizing the dialyzate to remove the reaction medium.

Step 4: Diazotization

In this step the antigen - PABA conjugate obtained from step 3 is diazotized at the PABA amine under conventional diazotizing conditions. Some exemplary conditions follow.

Two aqueous solutions are prepared at 0° to 5°C. One is a solution of the carrier-PABA conjugate acidified with HCl to a pH of from about 0.5 to 2.0, preferably from 1.0 to 1.5. The concentration is dictated by convenience and solubility, being from about 0.1 to 10 percent by weight carrier-PABA, with of the order of 4 per cent being preferred. The other solution is a simple aqueous solution of sodium nitrite which can be, for example, a 1 percent solution.

At a temperature of from 0° to 5°C., the sodium nitrite solution is added dropwise to the antigen-PABA solution to an end point as determined by potassium iodide-starch paper. Excess nitrous acid is decomposed with sulfamic acid. Under the acid conditions, the diazonium compound forms the salt.

Step 5: Hapten Coupling

The hapten is dissolved in water or aqueous alcohol depending upon its solubility, as is well known in the art. The concentration is not critical, but approximately 0.1 weight per cent hapten is convenient. The pH is adjusted with NaOH to alkalinity, preferably from about 9 to 11.

The diazonium solution from step 4 is added, dropwise, to this hapten solution at a temperature maintained at from 0° to 5°C. To avoid side reactions, the pH is maintained by the addition of NaOH. The mixture is stirred for a moderate period of time, for example 20 minutes, to ensure that the reaction goes to completion.

Step 6: Separation

In most cases the hapten-antigen conjugate will be required in either a pure form or in a pure solution. Accordingly, it is necessary to separate the other reactants, particularly unreacted hapten, from it. When the hapten is a small molecule, for example, triiodothyronine or thyroxine, this can be done by dialysis against an alkaline solution. The residual solution may be useful as such or can be lyophilized to yield the solid hapten-antigen conjugate if desired.

On the other hand, if the hapten is a macromolecule, for example, a polypeptide, it may not pass through the dialysis membrane and some other separation technique may be necessary. One such technique is by means of a gel filtration separating column. Suitable gels are marketed under the name "Sephadex" by Pharmacia Fine Chemicals Inc., Piscataway, New Jersey. Other similar gels may be used. The histidyl group has two diazotizable sites at the carbon atoms on either side of the ring-NH-group. Similarly, the tyrosyl and thyronine have diazotizable sites on either side of the hydroxyl group. However, in the case of the histidyl group, the sites are asymmetric, and, although in diazotization, the site between the two nitrogen atoms will probably be preferred, it is nevertheless to be expected that isomeric products will be formed. Accordingly, separation of the isomers is generally desirable, for example, by column chromatography. However, where the hapten has a substantial number of peptide groups, separation may be difficult or impossible. It is presently believed, however, that the problem is not serious and that isomeric coupling of such compounds will not produce antigenically distinct characteristics.

Relative Proportions of the Reactants

In general, these are not critical but are chosen to approach stoichiometric ratios for the reactions involved, and can be adjusted for the best material utilization. Thus, for example, a proteinic antigen such as bovine serum albumin can have from 60 to 70 available amine groups and, accordingly, it is desirable to use a proportion of about 70 equivalents of PABA. To ensure full antigen utilization an excess of up to 10 equivalent per cent PABA is desirable. As mentioned, it is desirable to have a stoichiometric excess of carbodiimide to PABA. While from 0.5 to 2.0 equivalents of carbodiimide to PABA could be used, from 1.0 to 1.2 are preferred.

In general, the range of variations of proportions of reactants will be within the usual limits of what is reasonable, with proportions near stoichiometric ratios being preferred.

Preparation of Antibodies

These are raised in conventional manner by repeated multiple subcutaneous injections into animals. The antisera are recovered by bleeding and, depending upon the type of assay for which they are used, antibodies may or may not be separated and purified. Radioimmune assays can be made using the serum without purification. Suitable animals include rats, rabbits, goats, donkeys, and guinea pigs.

Assays

The antibodies raised can be used in any immunogenic assay, but radioimmune assays are preferred. They are carried out in conventional manner for a competitive binding assay.

Essentially, in such an assay, the target assay compound is allowed to compete with known quantities of a radioactively labeled isomer in binding to an antibody. From the change in proportion of labeled material bound, due to the competition of the target compound with the labeled material, for the antibody, the amount of target compound present can be calculated.

Following are examples of certain specific embodiments of preparation of the conjugate, and the conjugate itself, according to the present invention. These examples should be considered as illustrative, only, and not as limiting in any way the full scope of the invention as covered in the appended claims.

EXAMPLE 1 Diiodothyronine a. Preparation of BSA-PABA

To a solution of 500 mg. BSA in 20 ml. water is added a solution of 250 mg. PABA in 5 ml. of 0.01N sodium hydroxide. The pH is adjusted to 6.5. To this mixture is added 500 mg. carbodiimide [1-cyclohexyl-3-(2-morpholinoethyl)-carbodiimide metho-p-toluene sulfonate] and the mixture is stirred overnight at room temperature. The pH is readjusted to 6.5 with 2N HCl after about 2 hours. The solution is then dialyzed against 6L of 0.001N HCl with a pH of 3 for 6 days with daily changes of the acid solution. It is next dialyzed against 6L of normal saline solution (0.9% NaCl w/v) for 2 days with daily changes of the dialysis solution. It is then lyophilized and used in subsequent coupling reactions.

b. Coupling of GSA-PABA with 3,5-diiodothyronine 200 mg. BSA-PABA is dissolved in 5 ml. water and the pH is adjusted to 1-1.5 with 4N HCl. The solution is then cooled to 0°-5°C. and to it is added a cold (0°-5°C.) solution of sodium nitrite (15 mg.) in 0.5 ml. water to an end point with starch iodide paper. The diazonium salt solution is stirred at this temperature for 15–20 minutes. Excess nitrous acid is decomposed with a few crystals of sulfamic acid. The cold diazonium salt solution is added dropwise to a cold (0°-5°C.) solution of 150 mg. of 3,5-diiodothyronine in 20–25 ml. of an ethanol water (20:80) solution adjusted to pH 9-11 with 2N sodium hydroxide. During the addition, the pH is maintained between 9 and 11 with 2N sodium hydroxide and the temperature is maintained at 0°-5°C. After the addition is complete, the solution is stirred at 0°-5°C at pH 10.5 for 1 hour. It is then transferred to a dialysis tubing and dialyzed against 6L of 0.5% sodium carbonate for 6 days with daily changes of the sodium carbonate solution. It is next dialyzed against 6L of pH 7.4–7.6 sodium phosphate buffer for 4 days with daily changes of the buffer solution. The optical density of 280 nanometer was determined and compared with a standard of 1.4 for a 0.1 percent solution, to indicate protein concentration.

The hapten-antigen conjugate produced, BSA-benzoylazo3,5-diiodothyronine, is a novel, synthetic antigen useful in generating antibodies. Antibodies generated by it can be useful in assaying for triiodothyronine. It can be used either in the solution that remains after dialysis, or that solution can be lyophilized to isolate the compound.

EXAMPLE 2 Triiodothyronine

The procedure of Example 1 is followed using triiodothyronine in place of 3,5-diiodothyronine, with the modification that 200 mg. of the triiodothyronine material is used in place of the diiodothyronine material in view of the former's greater molecular weight.

The hapten-antigen conjugate produced, BSA-benzoylazo-3-triiodothyronine is a novel, synthetic antigen useful in generating antibodies. Antibodies generated by it can be useful in assaying thyroxine (tetraiodothyronine). It can be used either in the solution that remains after dialysis, or that solution can be lyophilized to isolate the compound.

EXAMPLE 3 GLUCAGON a. Polylysine-PABA

Polylysine-PABA is prepared using the method of Example 1a and substituting poly-1-lysine (MW 8,000–30,000, No. 71–120B Miles Lab. Inc., Kankakee, Ill.) for the BSA.

b. Coupling of Polylysine-PABA with Glucagon 10 mg. of polylysine-PABA is stirred in a beaker in an ice bath with 5 ml. of water. The pH is adjusted to 1.0 with 1N HCl. 0.1% sodium nitrite solution is added until an excess of nitrous acid is seen on potassium iodide starch paper. The pH is maintained between 1.0 and 1.75 with a few drops of 1.0N HCl and the mixture is stirred for 30 minutes. Excess nitrous acid is removed with a few crystals of sulfamic acid.

10 mg. of porcine glucagon (Lilly Lot No. GLF 599A) is stirred in a beaker with 10 ml. of water and the pH is adjusted to 11.0 with 2.0N NaOH, the solution going from cloudy to clear with the adjustment. The polylysine-PABA solution is added dropwise while adjusting the pH to from 10.0 to 10.5. The final pH is 10.3. The reaction mixture is stirred for 20 minutes and the pH is adjusted to 3.9 with 0.5N HCl. The mixture, in a quantity of approximately 20 ml. is then applied to a 30 by 200 mm. gel filtration column packed with G-75 Sephadex, and eluted with 1M acetic acid. The polylysine fraction is freeze-dried. The yield of poly-1-lysine benzoyl azoglucagon is 10.8 mg.

The poly-lysine benzoylazoglucagon is characterized both visually and by its antigenicity. Visually it is a yellowish, water-soluble powder at a neutral pH and somewhat pink at an alkaline pH, retaining its color, substantially unchanged, in solution of corresponding pH. During the course of the final coupling step, the light pink color becomes apparent, indicating that diazo coupling is taking place. The antigenicity is reported below.

c. Raising of Antibodies

Approximately 2 mg. doses of antigen (from b) in 0.1% aqueous solution with Freund's adjuvant are injected at multiple subcutaneous sites in rabbits. The injections are repeated at intervals according to known immunization procedure. The rabbits are bled at intervals and the active serum is collected and used without purification.

d. Radioimmunoassay

The radioimmunoassay is performed by incubating at 4°C. for 1 to 4 days a range of dilutions of antisera from c from 125 I-labeled glucagon prepared by iodination of glucagon using the method of Hunter and Greenwood, "Biochem.," 89, 114 (1963). Separation of the 125 I-glucagon from the other materials was carried out on a G-25 Sephadex column. The 125 I-glucagon has a radioactivity of 55 microcuries per microgram. A dextran charcoal solution is added and the solutions are incubated for 15 minutes at 4°C. and then sedimented by centrifugation at 3,000 rpm. for 15 minutes, still at 4°C.

The supernatant is decanted and the activities of 1 ml. aliquots are counted in a gamma counter. The addition of increasing amounts of unlabeled glucagon, while containing a fixed amount of 125 I-glucagon and of antiserum, results in a competitive inhibition of the 125 I-glucagon bound to the antibody.

The relationship of the amount of unlabeled glucagon added to inhibition of binding is as follows:

| Nanograms of unlabeled glucagon added | % Inhibition of binding of 125 I-glucagon to antibody |
|---|---|
| 0 | 0 |
| 0.5 | 13 |
| 5.0 | 68 |
| 50.0 | 91 |
| 500.0 | 100 |

Cross reactivities of the antiserum with other polypeptides and proteins are tabulated below:

| | |
|---|---|
| Gut glucagon | <0.002% |
| Insulin | <0.004% |
| Secretin | <0.23% |

The cross-reactivity is defined according to the methods of Abrahams as the relative quantity of cross-reactant to subject compound (in this case, glucagon)) that produces 50% inhibition, multiplied by 100 for percentage.

While various specific examples of the process and products of the present invention have been shown and described, these should be considered as illustrative only and not as limiting, in any way, the full scope of the invention as covered in the appended claims.

I claim:
1. A synthetic antigen of formula:

wherein the carrier is selected from the class consisting of proteins and synthetic proteins, and confers antigenicity, R''' is coupled to the carrier through a reactive group, the residue being substantially non-reactive, R''' being bonded to the aryl with up to three bonds, being substituted or unsubstituted, and having up to four rings and up to 20 aliphatic carbon atoms; and the hapten has the formula:

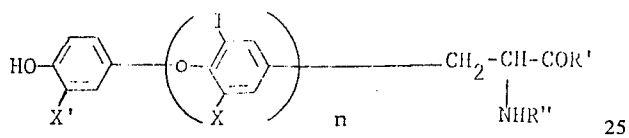

where R' is selected from the group consisting —OH and —NHP$_p$, and R'' is selected from the class consisting of —H and —COP$_p$, where P$_p$ is a polypeptide chain having from 1 to 250 peptide groups, with or without pendant groups; X is selected from the class consisting of H and I; X' is selected from the class consisting of H and I when X is I; $n$ is 0 or 1 and X' is H when $n$ is 0; bonding of the hapten to the diazo group being according to the direction of the ring members and substituents.

2. The synthetic antigen of claim 1 wherein the bond between the carrier and R''' is an amide bond.

3. The synthetic antigen of claim 1 wherein the carrier is a protein and the imine moiety of the amide is bound to the carrier, the carbonyl being bound to R'''.

4. The synthetic antigen of claim 1 wherein the carrier has a plurality of

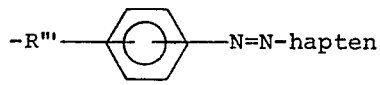

moieties bound thereto.

5. The synthetic antigen of claim 1 wherein the carrier is a protein selected from the class consisting of polylysine, bovine serum albumin, keyhole limpet hemocyanin, human immunogammaglobulin, and thyroglobulin.

6. The synthetic antigen of claim 1 wherein the hapten is:

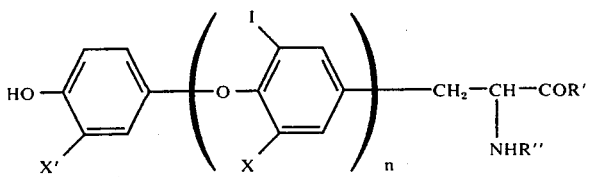

7. An antibody specific to the antigen of claim 1.
8. 3,5-Diiodothyronine azobenzoyl bovine serum albumin.
9. An antibody specific to the antigen of claim 8.
10. 3',3,5-Triiodothyronine azobenzoyl bovine serum albumin.
11. An antibody specific to the antigen of claim 10.
12. Poly-1-lysine benzoylazoglcagon.
13. An antibody specific to the antigen of claim 12.
14. The process of preparing the synthetic antigen of claim 1 comprising:
  1. mixing, in aqueous acid solution at a temperature of from −10°C. to 60°C., an antigenic protein and a primary aminoaryloic acid;
  2. adding a carbodiimide to the mixture of step (1) and reacting to produce an antigen-aminoaryloic conjugate;
  3. removing the unreacted reactants from the reaction product;
  4. separating the antigen-aminoaryloic conjugate from the residual reaction medium;
  5. diazotizing the amino group of the antigen-aminoaryloic conjugate by reaction in aqueous acid medium at a temperature of from 0° to 5°C.; and,
  6. adding the diazotized reaction product to an aqueous alkaline solution of the hapten, maintaining the reaction medium alkaline during the reaction, and stirring to complete the reaction.

15. The process of claim 14 wherein the removal of unreacted reactants is carried out by dialysis.
16. The process of claim 14 wherein the separation of the conjugate from the reaction medium is carried out by lyophilis.
17. A process for preparing an antigen of the formula:

wherein the carrier is selected from the class consisting of proteins and synthetic proteins, and confers antigenicity, R''' is coupled to the carrier through a reactive group, the residue being substantially non-reactive R''' being bonded to the aryl with up to three bonds, being substituted or unsubstituted, and having up to four rings and up to 20 aliphatic carbon atoms; and the hapten has the formula:

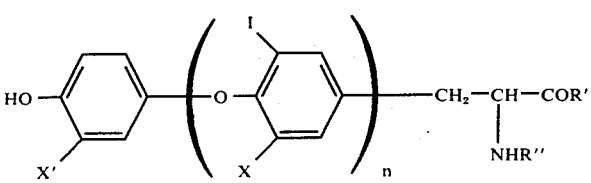

where R' is selected from the group consisting of -OH and -NHP$_p$, and R'' is selected from the class consisting of —H and —COP$_p$ where P$_p$ is a polypeptide chain having from 1 to 250 peptide groups, with or without pendant groups; X is selected from the class consisting of H and I; X' is selected from the class consisting of H and I when X is I; and $n$ is 0 or 1 and X' is H when $n$ is 0; comprising:
  a. conjugation of a primary aromatic amine with a carrier;
  b. separation of the reactants from step (a);
  c. lyophilization of the residue to remove the reaction medium;

d. diazotization of the residue; and, e. coupling of the hapten to the resulting product.

18. The process of claim 17 further comprising the removal of small molecular products of the amine conjugation step, prior to diazotization.

19. A method for forming a synthetic antigen from a carrier selected from the class consisting of proteins and synthetic proteins, said carrier having an available reactive group for coupling thereto, a hapten having a reactive group selected from the class consisting of amino and carboxyl, and a carbon atom susceptible to diazonium coupling, and a primary aromatic amine compound having a reactive residue capable of coupling to the reactive group on the carrier, wherein the carrier reactive group and the primary amine compound reactive residue consist of a carboxyl group and an amino group, whereby the carrier can be coupled to the primary amine compound by an amide group, the method comprising:

a. conjugation of the primary aromatic amine compound with the carrier to form an amide bond;

b. treatment of the conjugated primary aromatic amine compound to provide for bonding of the hapten by formation of diazonium ion; and c. coupling of the hapten to the conjugated diazonium ion.

20. The method of claim 19 wherein the carrier is a protein selected from the class consisting of polylysine, bovine serum albumin, keyhole limpet hemocyanin, human immunogammaglobulin, and thyroglobulin.

21. The method of claim 19 wherein the primary aromatic amine compound is para-aminobenzoic acid.

* * * * *